United States Patent [19]
Jacobssen

[11] Patent Number: 4,985,232
[45] Date of Patent: Jan. 15, 1991

[54] GASTRIC EMPTYING KIT
[75] Inventor: Patrick C. Jacobssen, Fairhope, Ala.
[73] Assignee: Insight Concept Innovation & Invention Center, Daphne, Ala.
[21] Appl. No.: 347,723
[22] Filed: May 5, 1989
[51] Int. Cl.$^5$ .................... A61B 6/00; B65D 69/00; A23C 1/06; A61M 36/14
[52] U.S. Cl. .................................. 424/4.1; 206/569; 426/385; 128/654; 128/659; 436/56
[58] Field of Search .......................... 426/385; 252/1; 424/1.1; 128/654, 659, 653 R; 206/569; 436/56, 57

[56] References Cited
U.S. PATENT DOCUMENTS

| | | |
|---|---|---|
| 3,264,121 | 8/1966 | Tuomy et al. .................. 426/385 X |
| 3,650,393 | 3/1972 | Reiss et al. ..................... 206/569 X |
| 3,768,979 | 10/1973 | Mead et al. . |
| 4,096,283 | 6/1978 | Rahman ......................... 426/385 X |
| 4,115,540 | 9/1978 | Digenis et al. . |
| 4,207,327 | 6/1980 | Lunsford et al. . |
| 4,243,652 | 1/1981 | Francis .............................. 424/1.1 |

OTHER PUBLICATIONS
"Scintigraphic Evaluation of Gastric Emptying", Leon S. Malmud et al., Seminars in Nuclear Medicine, No. 2 (Apr.), 1982.
Article Abstracts, Skagerberg et al., Vanlic-Razumenic N., Weiner et al., Datz et al., Corinaldesi et al., Patti et al.

Primary Examiner—John S. Maples
Attorney, Agent, or Firm—Nixon & Vanderhye

[57] ABSTRACT

A solid meal gastric emptying kit comprising:
(a) a first relatively small tagging container;
(b) a first package of freeze-dried meat for tagging with TC$^{99m}$ Sulfur Colloid;
(c) a second relatively large mixing and serving container;
(d) a second package containing a napkin, a towelette, and a plastic spoon;
(e) an absorbant pad;
(f) radioactive material labels; and
(g) instructions for preparation.

18 Claims, 1 Drawing Sheet

GASTRIC EMPTYING KIT

BACKGROUND AND SUMMARY OF THE INVENTION

The present invention relates to radiodiagnostic test procedures in the clinical analysis of the gastrointestinal tract and, more specifically, to a gastric emptying kit for use in such procedures.

Various techniques for clinically testing the gastrointestinal tract are known, some of which involve the use of radioactive material. Technitium $99^m$ is a commonly used radionuclide in nuclear medicine because of its favorable imaging characteristics. See, for example, U.S. Pat. No. 4,115,540.

A known gastro emptying procedure utilizing radioactive material in solid food is disclosed in U.S. Pat. No. 4,207,327. Also see *Scintigraphic Evaluation of Gastric Emptying* by Leon Malmud, Robert S. Fisher, Linda C. Knight and Elizabeth Rock; *Seminars in Nuclear Medicine*, Vol. XII, No. 2 (April, 1982), the text of which is incorporated herein by reference.

The known gastric emptying test procedures are not particularly favored by technologists and physicians at the present time because of a lack of overall standardization. For example, in the present practice, a technician must procure a specially prepared meal on the day of the examination. This, of course, creates difficulties in obtaining exact comparisons of a patient's most recent test with previous tests done at the same or other hospital. Studies of a variety of gastric disorders require that the test procedure be exactly the same, each time it is conducted. For example, in the $I^{131}$ Hippuran Renogram, where blood and urine samples are taken at specific times and compared to an exact calculated standard, precise information is an absolute necessity.

The known procedures are also regarded as time consuming and messy, and involve the troublesome issue of waste disposal.

The present invention eliminates the above described problems by providing a standardized test package in kit form which includes everything necessary to perform the test with the exception of radioactive material, which is provided separately.

In one exemplary embodiment of the invention, a kit is provided which contains a package of freeze dried beef as the solid meal tracer. As will be explained in greater detail below, freeze dried beef was chosen because of its good labeling efficiency, i.e., it holds the radioactive material better than other previously used solid foods, and it does not dissociate into liquid during testing. In addition, the use of freeze dried, pre-cooked beef enhances standardization, and is easy to prepare. Freeze dried beef is also preferred by many people over previously used solid foods such as chicken livers and/or scrambled eggs.

The kit in accordance with this invention also contains one (1) small plastic container provided with injection port means; one (1) large plastic combination mixing and serving container; one (1) can of beef stew; one (1) package containing a napkin, radiacwash towelette and plastic spoon (for mixing and serving); one (1) plastic bag for containment and disposal of radioactive waste; one (1) absorbant pad for patient use; radioactive material labels; and instructions for preparation.

A further aspect of the invention relates to a procedure for preparing and carrying out a gastric emptying process utilizing the above described kit. In an exemplary embodiment, the process includes the steps of:

(a) cutting open the package of freeze dried beef; placing a portion of the beef in the small tagging container until level with a black line indicated on the side of the container; placing a top on container, and discarding the unused portion of the beef.

(b) with a sterile lead-shielded 30 cc syringe, aseptically obtaining one (1) millicurie of $Tc^{99m}$ Sulfur Colloid;

(c) using the same 30 cc syringe of Sulfur Colloid, drawing up the remaining volume of the syringe with warm sterile water;

(d) behind lead shielding, injecting the 30 cc Sulfur Colloid 1mCi) and warm sterile water into the small tagging container containing the freeze-dried beef via the injection port, and labeling the container as radioactive;

(e) allowing about five minutes for the radioactive material to be absorbed into the meat, while occasionally shaking the container to insure even distribution;

(f) after making sure that all the liquid has been absorbed, carefully opening the small tagging container and pouring the radio-labeled beef into the large plastic serving container;

(g) opening the can of beef stew provided, and carefully adding it to the serving container of the now radioactive labeled beef;

(h) placing the container in a microwave oven for approximately one minute, or until warm;

(i) stirring with the plastic serving utensil and then serving it to the patient;

(j) placing all contaminated materials into the plastic bag provided, storing in a shielded area until residual activity has decayed to background level, and thereafter disposing of the bag and its contents.

The gastric emptying kit in accordance with this invention has the following advantages:

1. One Convenient Package: With the exception of the radioactive isotope, all the items necessary to perform the gastric emptying procedure are contained in one package.

2. Ease of Preparation: This kit is as easy to prepare as most other radiopharmaceuticals. No cooking is required. Just warm and serve.

3. Reduced Isotopic Contamination: This procedure, which uses dried beef, compared to other solid meals now being used (e.g., scrambled eggs and chicken livers) reduces possible contamination because of two of the main features of this kit, Item 2 above and Item 7 below. When the actual time required in dealing with the isotope itself is reduced, so also will the radiation risk to the technologist. This radiation safety factor is in itself a very advantageous feature.

4. High Patient Acceptability: Most people surveyed prefer roast beef over scrambled eggs or chicken livers.

5. Standardization of Gastric Testing: The ease of preparation, and the exact meal amounts in each kit allows the test to be reproduced accurately and efficiently. Patients can thus be rescanned many times without the worry of differences in preparation, meal types, or amounts—all of which would affect gastric emptying times.

6. Long Shelf Life: Since freeze dried meat can be stored for long periods, the kit of this invention can be stored on the shelf until ready for use. This eliminates the necessity of procuring a solid meal on the day of the examination.

7. Easy Clean-Up: Everything contained in the Gastrotec Kit is disposable. All contaminated containers and utensils can be placed in the plastic bag provided and stored in a designated waste area for a few days. When the waste has decayed to an acceptable background level, it can then be surveyed and disposed of in normal trash.

Additional objects and advantages will become apparent from the detailed description which follows.

BRIEF DESCRIPTION OF THE DRAWINGS

The sole FIGURE is an exploded view of the kit and its contents in accordance with an exemplary embodiment of the invention.

DETAILED DESCRIPTION OF THE DRAWING

Figure 1:
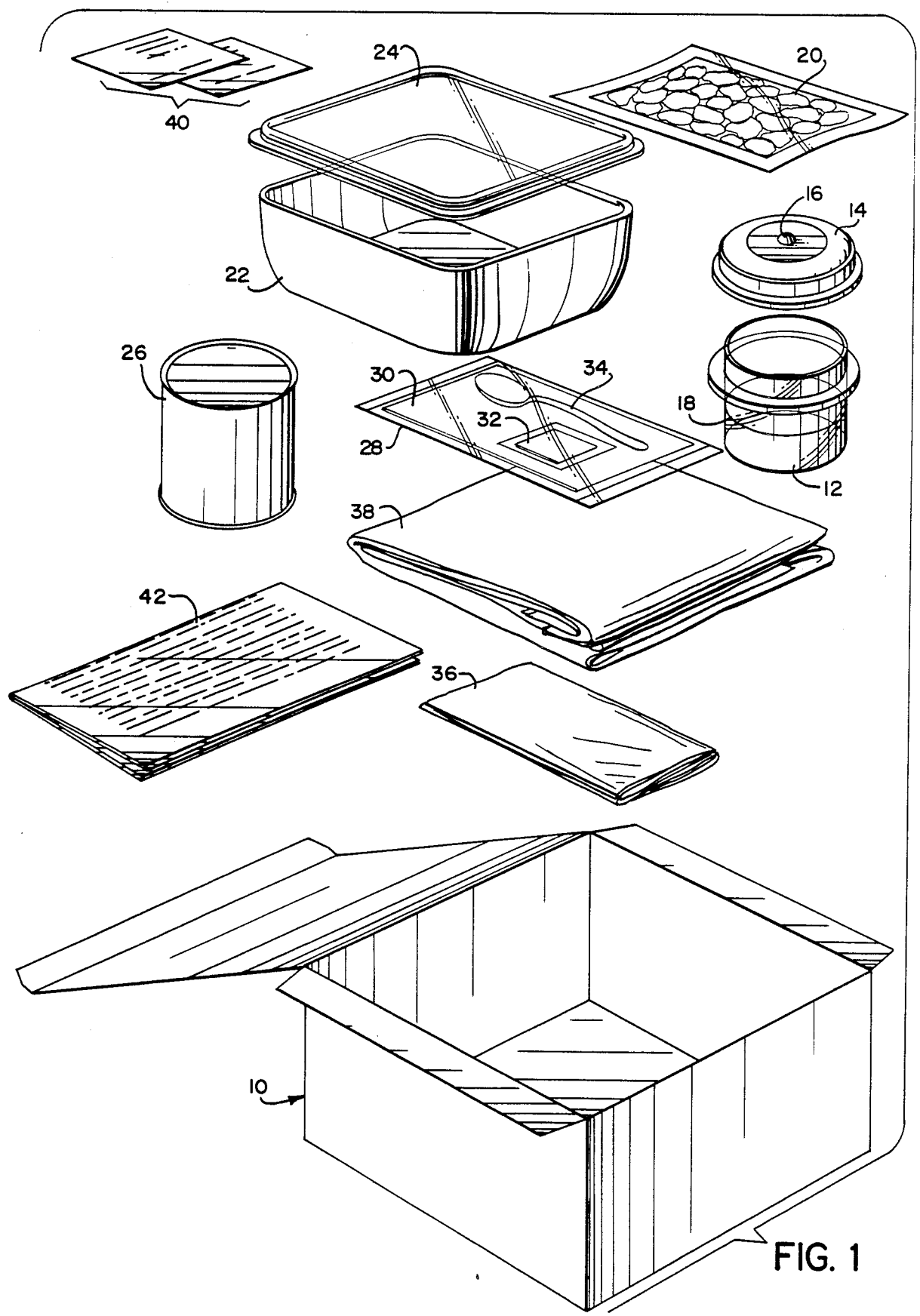

With reference now to the FIGURE, a kit enclosure or box 10 is illustrated which may be of any suitable configuration, and preferably constructed of cardboard or paperboard material. The composition as well as the configuration of the kit enclosure is variable, e.g., plastic may also be used, and suitable shapes include rectangular, square, cylindrical, etc. with the principal objective being a simple, compact and lightweight construction, preferably capable of being stacked.

The kit enclosure 10 may also be provided with interior partitions (not shown) to compartmentalize the enclosure for organizing the contents, but this is not essential. The kit contents include a first relatively small container 12, preferably made of plastic material, and provided with a suitable, removable lid or cover 14. The lid 14 is preferably of the snap-on type, although other configurations may be utilized as well, so long as a substantially liquid tight relationship is effected between the lid and the container.

The container lid 14 is also provided with an injection port 16 which may comprise a resilient rubber plug or the like, and which facilitates the injection of a radioactive material into the container as described in greater detail below. The container 12 is also provided with an indicator mark 18 which indicates a level to which freeze dried beef is added to the container in the test procedure preparation process.

The kit 10 also includes a relatively small package 20 of freeze dried beef for tagging with $TC^{99m}$ Sulfur Colloid. Freeze dried beef has been chosen as the solid meal tracer for incorporation into the kit of this invention for a variety of reasons. For example, freeze dried beef has been determined to hold its labeling of radioactive material longer than other solid food tracers utilized in the gastric emptying field. In this regard, a quality control study was performed on freeze-dried beef in accordance with a quality control procedure as outlined in the above-identified Malmud article. The results of this study showed that the labeling of freeze-dried beef was of equal or better quality as any of the previously used solid food tracers. More specifically, labeled samples of freeze-dried beef placed in the gastric juice for one hour, without a water bath, showed that the beef held 97% of its radioactive material. Labeled samples placed in gastric juice, as well as in a water bath for three hours, showed that they retained 94% of their radioactive material.

Freeze-dried beef was also chosen because, after the beef is injected with radioactive material, it is absorbed directly into the meat itself so that little or no dissociation from solid to liquid during the testing procedure is experienced.

In addition, freeze dried beef is easily maintained until ready for use, and is easily prepared since it is precooked and therefore requires only warming. A further advantage of freeze-dried beef lies in the simple fact that more people prefer the taste of beef over the previously employed chicken livers and/or scrambled eggs.

A second larger plastic container 22 is also provided, and includes a removable lid 24 which may also be of the snap-on type. The container 22 is utilized for mixing the radioactive freeze-dried beef with an additional food product, preferably beef stew, as provided in a conventional can 26.

An additional package 28, which may be of a simple plastic bag configuration, has sealed therein a napkin 30, a radiacwash towelette 32 and a plastic utensil, such as a spoon 34, all of which are sealed within the package 28.

Also enclosed within the kit enclosure 10 is a plastic waste bag 36, an absorbant pad 38 for patient use, and a plurality (preferably three) of radioactive material labels 40.

Each of the above items are designed to fit easily within the enclosure 10 and all of the above contents have the characteristic of long shelf life so that the kits in accordance with this invention may be stored on shelves within hospitals, clinics, etc. over extended periods of time until just prior to use.

In a preferred procedure for preparing and using the kit, the lab technician or physician, preferably wearing waterproof latex gloves, first cuts open the package of freeze-dried beef and places a portion of the beef in the small tagging container 12 to the level indicator 18 located on the side of the container. The lid 14 is then placed on the container and the unused portion of beef 20 may be discarded. Subsequently, and with the use of a sterile lead shield 30 cc syringe, the technician or physician aseptically obtains one millicurie of $TC^{99m}$ Sulfur Colloid, and using the same syringe, draws up the remaining volume of the syringe with warm, sterile water. Again, using the lead shielding, the technician or physician then injects the 30 cc of Sulfur Colloid and warm sterile water into the small tagging container 12 containing the freeze-dried beef 20 via the injection port 16.

Sufficient time, preferably about five minutes, is then allotted for the radioactive material to be absorbed into the freeze-dried beef 20, and occasional shaking during this period of time facilitates even distribution of the radioactive material.

Thereafter, the technician or physician opens the small tagging container 12 and pours the contents thereof into the second larger plastic container 22. The beef stew from can 26 is then added to the second larger container 22 and the container 22 is thereafter warmed, for example, in a microwave oven for approximately one minute, and then stirred with a plastic utensil such as the spoon 34. The preparation is then served to the patient.

After the test procedure has been completed, all of the remaining materials are placed into the plastic waste bag 36 and stored in a shielded area until all residual radioactive activity has decayed to an acceptable background level. The bag may then be disposed of in a conventional manner.

As will be appreciated by those skilled in the art, the kit and related process of this invention provides a measure of simplicity heretofore unobtainable with known gastric emptying test procedures. More specifically, the simplicity and ease of use of the kit will attract both technologists and physicians in research hospitals, and community institutions to make much more consistent use of this valuable diagnostic procedure. In addition, utilization of the kit in accordance with this invention will clearly standardize the results derived from gastric emptying tests. Such standardization is critical to the integrity of the test procedure, and is a most significant feature of this invention.

The economic benefits already mentioned, i.e., minimal manufacturing costs, and long shelf life add to the appeal of the kit.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A solid meal gastric emptying kit for use in a standardized nuclear gastric imaging procedure comprising:
   (a) a first container and associated lid;
   (b) a package of freeze-dried beef for tagging with a radioactive isotope;
   (c) a second mixing and serving container; and
   (d) a can of food for mixing with the freeze-dried beef, wherein said lid is further provided with resilient injection port means for receiving an injection of said radioactive isotope upon placement of said freeze-dried beef in said first container.

2. The kit according to claim 1 wherein said can of food comprises a can of beef stew.

3. The kit according to claim 1 and further comprising a sealed package including at least one utensil.

4. The kit according to claim 1 and further including radioactive material labels.

5. The kit according to claim 1 and further including instructions for preparation.

6. The kit according to claim 1 wherein said injection port means comprises a resilient plug mounted in said lid of said first container.

7. The kit according to claim 1 wherein said first and second containers are plastic.

8. The kit according to claim 1 and further including a third container for containment and disposal of radioactive waste.

9. The kit according to claim 8 wherein said third container comprises a plastic bag.

10. The kit according to claim 1 wherein said first container includes indicator means for indicating the predetermined amount of freeze dried beef to be added thereto.

11. A solid meal gastric emptying kit for use in a standardized nuclear gastric imaging procedure comprising:
    (a) a first tagging container;
    (b) a first packaging of freeze-dried meat for tagging with $TC^{99m}$ Sulfur Colloid:
    (c) a second mixing and serving container;
    (d) a second package containing a napkin, a towelette, and a plastic spoon;
    (e) an absorbant pad;
    (f) radioactive material labels; ad
    (g) instructions for preparation.

12. A solid meal gastric emptying kit for use in a standardized nuclear gastric imaging procedure comprising:
    (a) a package of freeze-dried beef for tagging with a radioactive isotope;
    (b) a first container for holding at least a portion of said freeze-dried beef during tagging with said radioactive isotope;
    (c) a second mixing and serving container;
    (d) a can of food for mixing with the freeze-dried beef; and
    (e) a plurality of radioactive material labels.

13. The kit according to claim 12 wherein said can of food comprises a can of beef stew.

14. The kit according to claim 12 and further comprising a sealed package including at least one utensil.

15. The kit according to claim 12 and further including a third container for containment and disposal of radioactive waste.

16. The kit according to claim 12 and further including instructions for preparation.

17. The kit according to claim 12 wherein said first relatively small tagging container is provided with injection port means facilitating injection of said radioactive isotope.

18. The kit according to claim 12 wherein said first container includes indicator means for indicating the predetermined amount of freeze-dried beef to be added thereto.

* * * * *